(12) United States Patent
Sung

(10) Patent No.: US 8,184,821 B2
(45) Date of Patent: May 22, 2012

(54) ACOUSTIC TRANSDUCER DEVICE

(75) Inventor: Po-Hsun Sung, Tainan (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 1151 days.

(21) Appl. No.: 12/021,220

(22) Filed: Jan. 28, 2008

(65) Prior Publication Data

US 2009/0190771 A1 Jul. 30, 2009

(51) Int. Cl.
*G10K 11/16* (2006.01)
*A61F 11/06* (2006.01)

(52) U.S. Cl. ........ 381/71.6; 381/380; 381/382; 181/196

(58) Field of Classification Search ................ 381/71.1, 381/71.6, 328, 380, 382; 181/129–135, 196–198
See application file for complete search history.

(56) References Cited

U.S. PATENT DOCUMENTS

| | | | |
|---|---|---|---|
| 2,184,891 A * | 12/1939 | Bourne | ........................ 181/273 |
| 4,455,675 A | 6/1984 | Bose et al. | |
| 4,985,925 A | 1/1991 | Langberg et al. | |
| 5,668,883 A | 9/1997 | Abe et al. | |
| 5,832,094 A | 11/1998 | Le Her | |
| 6,683,965 B1 | 1/2004 | Sapiejewski | |

* cited by examiner

*Primary Examiner* — Ramon Barrera
(74) *Attorney, Agent, or Firm* — Finnegan, Henderson, Farabow, Garrett & Dunner, LLP

(57) ABSTRACT

A noise attenuation device comprising a first tube for receiving an acoustic signal, a first housing defining a first cavity between a first surface and a second surface, the first tube being coupled to the first housing at the first surface for conducting the acoustic signal into the first cavity, wherein one end of the first tube contacts the first surface at a first region with a first area, a second housing defining a second cavity between a first surface and a second surface, and a second tube coupled between the second surface of the first housing and the first surface of the second housing for conducting the acoustic signal between the first cavity and the second cavity, wherein one end of the second tube contacts the second surface of the first housing at a second region with a second area, wherein the first tube, the first housing and the second tube form a filter structure and the area of the first surface of the first housing is greater than the first area and the area of the second surface of the first housing is greater than the second area.

22 Claims, 12 Drawing Sheets

ACOUSTIC TRANSDUCER DEVICE

BACKGROUND OF THE INVENTION

The present invention generally relates to a noise attenuation device and, more particularly, to an acoustic transducer device for noise attenuation.

Remarkable technological advances render the prevalence of various electronic products. Consumer electronic products, especially portable multi-media products, may provide real-time audio and video contents of interest. Most of the multi-media products are generally equipped with at least one speaker to give off sounds. However, since users may not clearly hear the sounds from speakers due to ambient noise, consequently, headphones or earphones, which may be capable of attenuating ambient noise, are widely used in conjunction with speakers for audio signal transmission.

A headphone may be designed to surround and cover the outer ears of a user to isolate ambient noise. For example, headphones may be devised to exert force against the ears so as to seal the ears tight and provide noise isolation. However, the pressure on the ears of a user may cause a phenomenon of autophony, which may make the user uneasy or uncomfortable. Furthermore, some headphones may have a large size and thus may cause inconvenience to their users.

Earphones are able to fit the auditory canals of ears so that ambient noise may be blocked outside. Moreover, a noise reduction circuit may be used in an earphone to compensate for noise at a low frequency range from approximately 16 Hertz (Hz) to 1 kilohertz (kHz). Nevertheless, such a noise reduction circuit may not process noise at a high frequency range over approximately 1 kHz. High-frequency noise, however, may also be sensed by the ears and interfere with audio signals of interest.

Therefore, it may be desirable to have an acoustic transducer device that is able to efficiently transmit audio signals and attenuate ambient noise.

BRIEF SUMMARY OF THE INVENTION

Examples of the present invention may provide a noise attenuation device comprising a first tube for receiving an acoustic signal, a first housing defining a first cavity between a first surface having an area and a second surface having an area, the first tube being coupled to the first housing at the first surface for conducting the acoustic signal into the first cavity, wherein one end of the first tube contacts the first surface at a first region with a first area, a second housing defining a second cavity between a first surface and a second surface, and a second tube coupled between the second surface of the first housing and the first surface of the second housing for conducting the acoustic signal between the first cavity and the second cavity, wherein one end of the second tube contacts the second surface of the first housing at a second region with a second area, wherein the first tube, the first housing and the second tube form a filter structure and the area of the first surface of the first housing is greater than the first area and the area of the second surface of the first housing is greater than the second area.

Some examples of the present invention may also provide a noise attenuation device comprising a noise processing device comprising a first tube for receiving an acoustic signal, a first housing defining a first cavity between a first surface having an area and a second surface having an area, the first tube being coupled to the first housing at the first surface for conducting the acoustic signal into the first cavity, wherein one end of the first tube contacts the first surface at a first region with a first area, a second housing defining a second cavity between a first surface and a second surface, and a second tube coupled between the second surface of the first housing and the first surface of the second housing for conducting the acoustic signal between the first cavity and the second cavity, wherein one end of the second tube contacts the second surface of the first housing at a second region with a second area, wherein the area of the first surface of the first housing is greater than the first area and the area of the second surface of the first housing is greater than the second area so as to attenuate noise in the second cavity, a first microphone, a speaker electrically coupled to the second housing, and a signal processing circuit electrically coupled to the first microphone and the speaker.

Examples of the present invention may further provide a noise attenuation device comprising at least one first tube for receiving an acoustic signal, a first housing defining a first cavity between a first surface having an area and a second surface having an area, the at least one first tube being coupled to the first housing at the first surface for conducting the acoustic signal into the first cavity, wherein one end of each of the at least one first tube contacts the first surface of the first housing at a first region with a first area, a second housing defining a second cavity between a first surface and a second surface, and at least one second tube coupled between the second surface of the first housing and the first surface of the second housing for conducting the acoustic signal between the first cavity and the second cavity, wherein one end of each of the at least one second tube contacts the second surface of the first housing at a second region with a second area, wherein the area of the first surface of the first housing is greater than a sum of the first area of each of the at least one first tube and the area of the second surface of the first housing is greater than a sum of the second area of each of the at least one second tube to attenuate noise over a predetermined frequency level.

BRIEF DESCRIPTION OF THE SEVERAL VIEWS OF THE DRAWINGS

The foregoing summary as well as the following detailed description of the preferred embodiments of the present invention will be better understood when read in conjunction with the appended drawings. For the purposes of illustrating the invention, there are shown in the drawings embodiments which are presently preferred. It is understood, however, that the invention is not limited to the precise arrangements and instrumentalities shown. In the drawings.

DETAILED DESCRIPTION OF THE INVENTION

Reference will now be made in detail to the present examples of the invention illustrated in the accompanying drawings. Wherever possible, the same reference numbers will be used throughout the drawings to refer to the same or like portions. It should be noted that the drawings are in simplified form and are not drawn to precise scale. In reference to the disclosure herein, for purposes of convenience and clarity only, directional terms such as inner, outer, upper and lower, are used with respect to the accompanying drawings. Such directional terms used in conjunction with the following description of the drawings should not be construed to limit the scope of the invention in any manner not explicitly set forth in the appended claims.

Figure 1A:
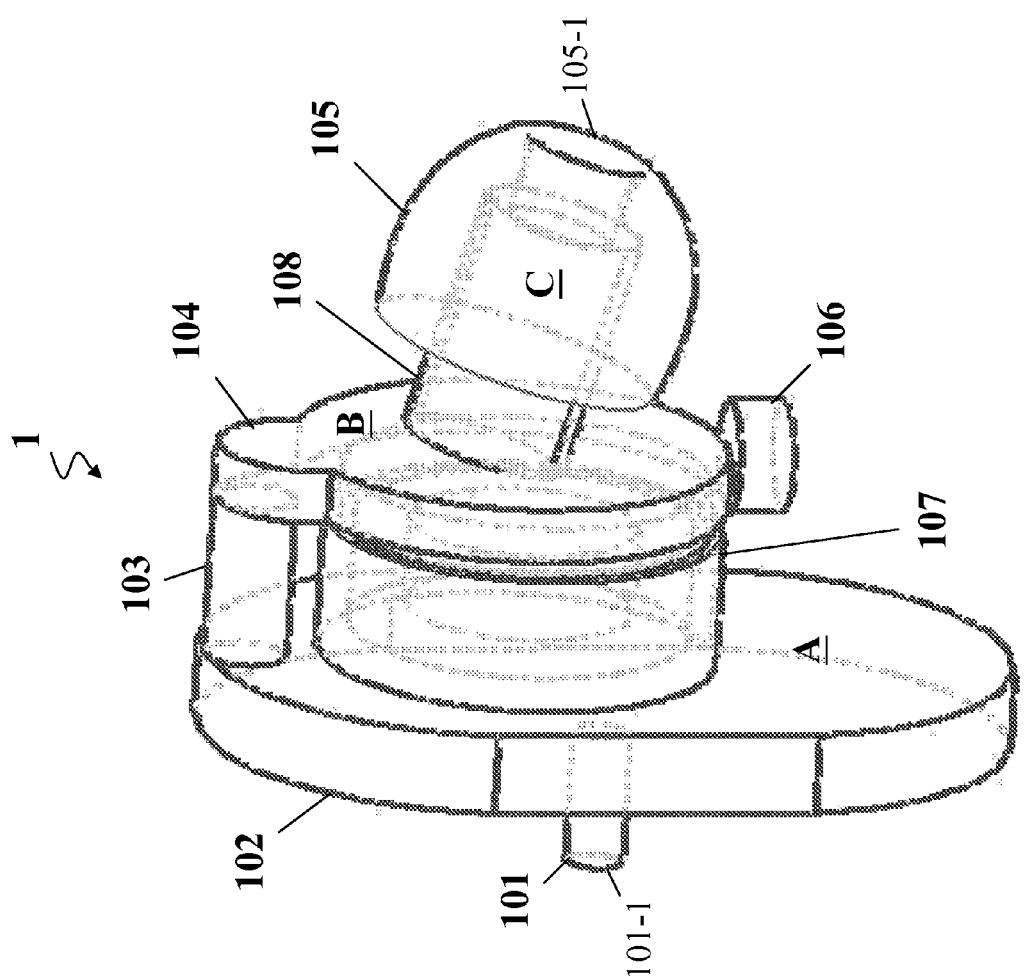
FIG. 1A is a diagram illustrating an assembly of a noise attenuation device in accordance with an example of the present invention.

FIG. 1A is a diagram illustrating an assembly of a noise attenuation device 1 in accordance with an example of the present invention. Referring to FIG. 1A, the noise attenuation device 1 may include a first tube 101, a first housing 102, a second tube 103, a second housing 104, an earplug 105, a microphone 106, a speaker 107 and a third tube 108. The first housing 102 and the second housing 104 respectively define therein a first cavity "A" and a second cavity "B". The first tube 101 may be coupled to the first housing 102, which in turn may be coupled to the second tube 103 and then the second housing 104. The earplug 105 may include an inner cavity "C" to tightly surround and encompass the circumference of the third tube 108, and one or more opening 105-1 to contact the ear canal of a user. Accordingly, an audio channel extending from a first end 101-1 of the first tube 101 through the first cavity A, the second tube 103, the second cavity B and the third tube 108 to the opening 105-1 of the earplug 105 may be formed in the noise attenuation device 1. The microphone 106 and the speaker 107 may be disposed near the second housing 104. In the present example, the microphone 106 may be disposed under the second housing 104. Furthermore, the speaker 107 may be disposed between the first housing 102 and the second housing 104.

Figure 1B:
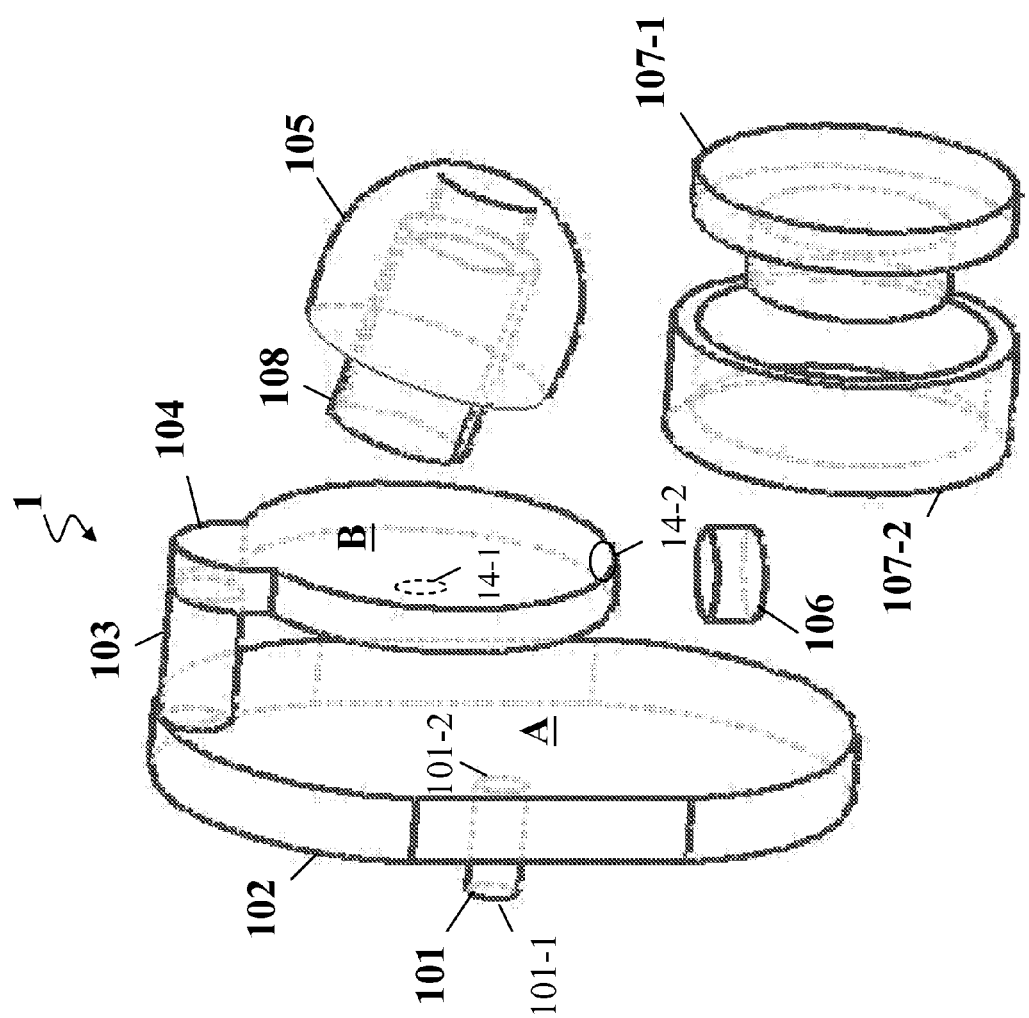
FIG. 1B is an exploded view of the noise attenuation device described and illustrated with reference to FIG. 1A.

FIG. 1B is an exploded view of the noise attenuation device 1 described and illustrated with reference to FIG. 1A. Referring to FIG. 1B, the speaker 107 may include a speaker body 107-1 and a speaker chamber 107-2, which in turn may respectively serve as a receiver and a back chamber for the speaker 107. In the present example, one or more first opening 14-1 may be provided in the second housing 104 to receive acoustic signals from the speaker 107. The acoustic signals may then be transmitted through the cavity B and the third tube 108 toward the earplug 105. Furthermore, when the microphone 106 is disposed under the second housing 104 as illustrated in FIG. 1A, one or more second opening 14-2 may be provided in the second housing 104 to facilitate the microphone 106 to receive the acoustic signals in the cavity B. In another example of the present invention, the microphone 106 may be disposed on an outer wall of the second housing 104. In yet another example of the present invention, the microphone 106 may be disposed within the second housing 104. In still another example, more than one microphone 106 may be used to receive the acoustic signals in the cavity B.

Figure 1C:
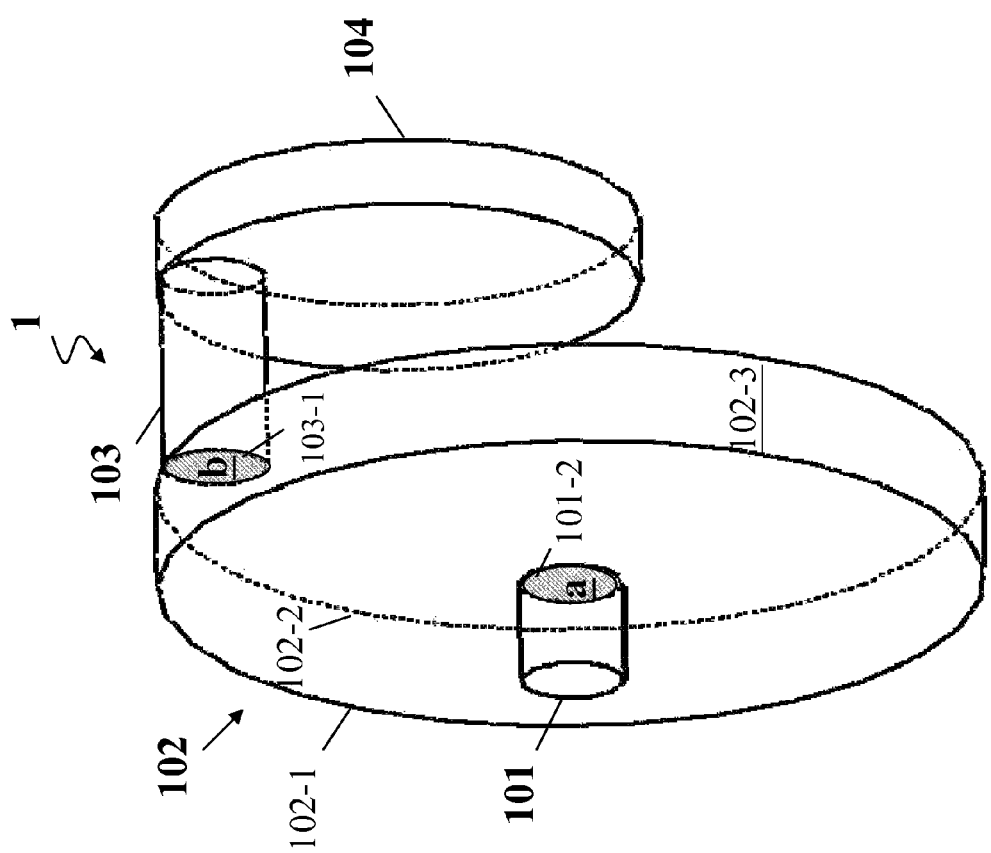
FIG. 1C is a perspective view of portions of the noise attenuation device illustrated in FIG. 1A.

FIG. 1C is a perspective view of portions of the noise attenuation device 1 illustrated in FIG. 1A. Referring to FIG. 1C, the first housing 102 and the second housing 104 may have a cylindrical shape. The first tube 101 may be disposed near or at the center of a first outer wall 102-1 of the first housing 102. The second tube 103 may be coupled between upper portions of the first and second housings 102 and 104. In an example of the present invention, a second end 101-2 of the first tube 101 may contact the outer wall 102-1 at a first region "a" with a first area, and a first end 103-1 of the second tube 103 may contact a second outer wall 102-2 at a second region "b" with a second area. The first outer wall 102-1, the second outer wall 102-2 and a sidewall 102-3 may together define therein the cavity "A". In one example, the area of the first outer wall 102-1 may be greater than the first area, and the area of the second outer wall 102-2 may be greater than the second area. Furthermore, the ratio of the area of the first outer wall 102-1 to the first area may range from approximately 30 to 300. The first tube 101 and the second tube 103 may be approximately 1 millimeter (mm) in length but may be longer or shorter. Furthermore, the first housing 102 and the second housing 104 may be approximately 1 mm in width but may be thinner or thicker. The volume of the cavity B enclosed by the second housing 104 may be kept relatively small to facilitate miniature of the noise attenuation device 1.

Figure 1D:
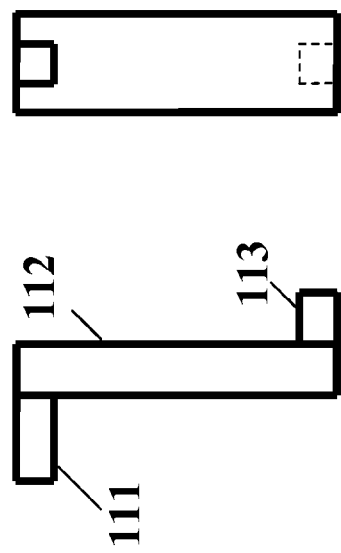
FIGS. 1D, 1E and 1F each show a side view and a rear view of a noise attenuation device in accordance with an example of the present invention.
Figure 1E:
Figure 1E:
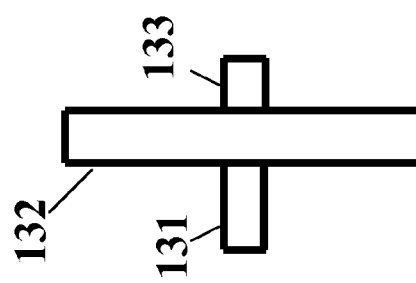
Figure 1F:
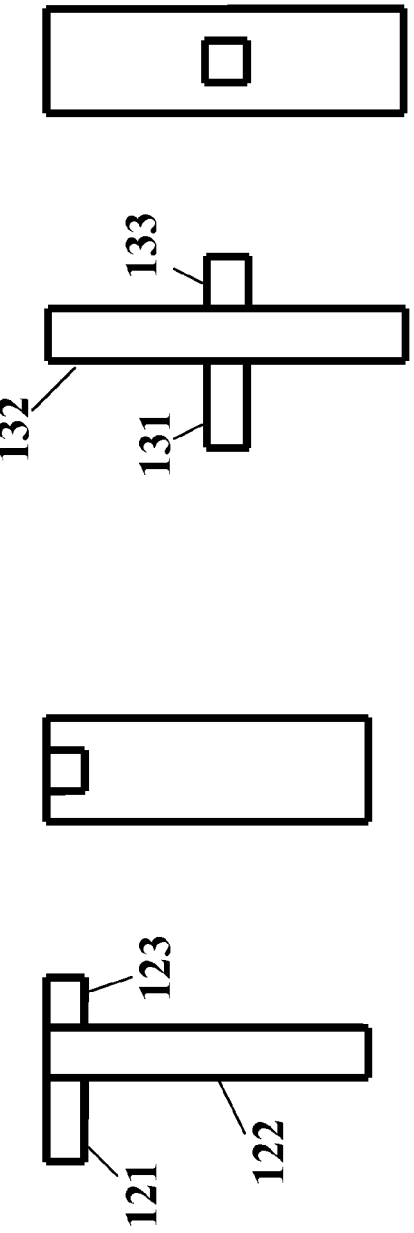

FIGS. 1D, 1E and 1F each show a side view and a rear view of a noise attenuation device in accordance with an example of the present invention. For simplicity, a second housing similar to the second housing 104 in FIG. 1C is not illustrated. Referring to the left part of FIG. 1D, which illustrates a side planar view of an arrangement, the noise attenuation device may include a first tube 111, a first housing 112 and a second tube 113. The first tube 111, the first housing 112 and the second tube 113 may respectively be similar to the first tube 101, the first housing 102 and the second tube 103 described and illustrated with reference to FIG. 1C except that, for example, the first tube 111 may be disposed near an upper portion of the first housing 112 and the second tube 113 may be disposed near a lower portion of the first housing 112. Referring to the right part of FIG. 1D, a rear view of the arrangement of the noise attenuation device is illustrated.

Referring to FIG. 1E, the noise attenuation device may include a first tube 121, a first housing 122 and a second tube 123. The first tube 121, the first housing 122 and the second tube 123 may respectively be similar to the first tube 101, the first housing 102 and the second tube 103 described and illustrated with reference to FIG. 1C except that, for example, the first tube 121 may be coupled to an upper portion of the first housing 122.

Referring to FIG. 1F, the noise attenuation device may include a first tube 131, a first housing 132 and a second tube 133. The first tube 131, the first housing 132 and the second tube 133 may respectively be similar to the first tube 101, the first housing 102 and the second tube 103 described and illustrated with reference to FIG. 1C except that, for example, the first tube 131 and the second tube 133 may be coupled to a center portion of the first housing 132.

Figure 1G:
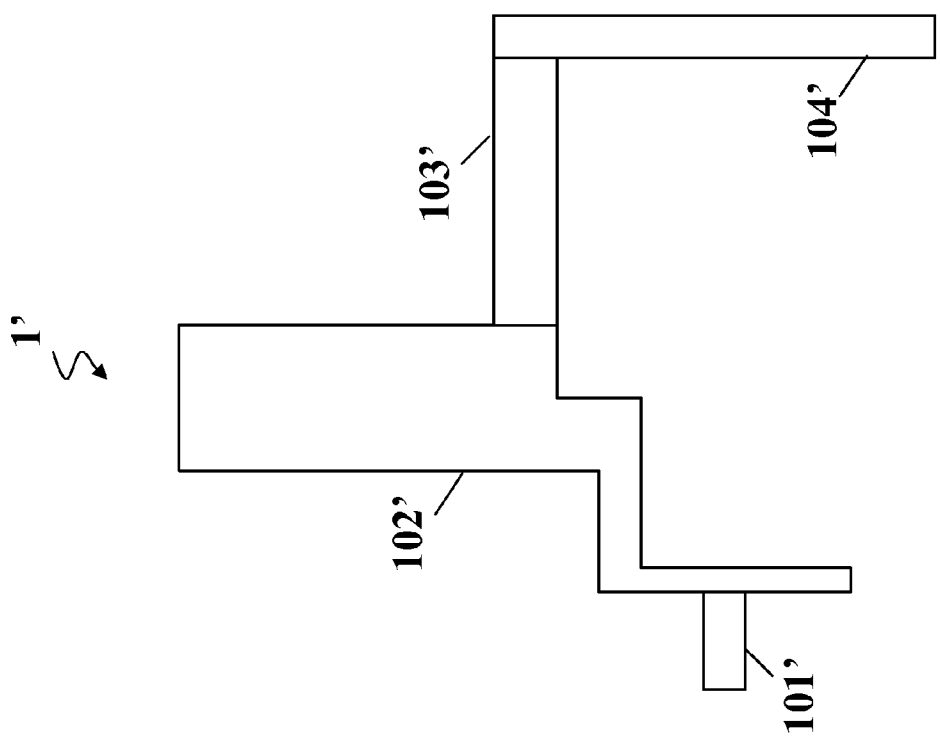
FIG. 1G is a schematic diagram illustrating a portion of a noise attenuation device in accordance with another example of the present invention.

FIG. 1G is a schematic diagram illustrating a portion of a noise attenuation device 1' in accordance with another example of the present invention. Referring to FIG. 1G, the noise attenuation device 1' may include a first tube 101', a first housing 102', a second tube 103' and a second housing 104'. The noise attenuation device 1' may be similar to the noise attenuation device 1 described and illustrated with reference to FIG. 1A except that, for example, one or both of the first housing 102' and the second housing 104' may have an irregular shape rather than a cylindrical shape.

Figure 2A:
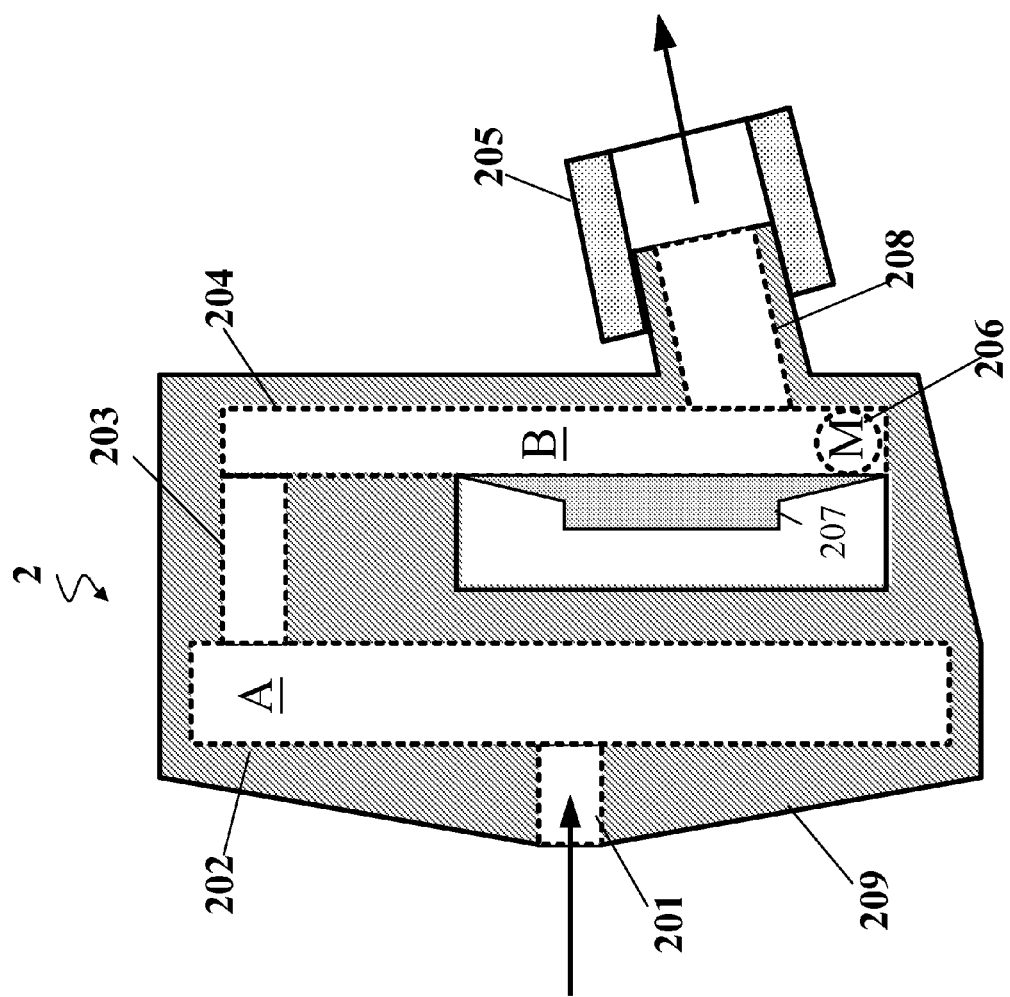
FIG. 2A is a cross-sectional diagram of a noise attenuation device in accordance with an example of the present invention.

FIG. 2A is a cross-sectional diagram of a noise attenuation device 2 in accordance with an example of the present invention. Referring to FIG. 2A, the noise attenuation device 2 may include a first tube 201, a first housing 202, a second tube 203, a second housing 204, an earplug 205, a microphone 206, a speaker 207 and a third tube 208. The noise attenuation device 2 may be similar to the noise attenuation device 1 described and illustrated with reference to FIG. 1A except that, for example, the microphone 206 may be disposed within the second housing 204.

Figure 2B:
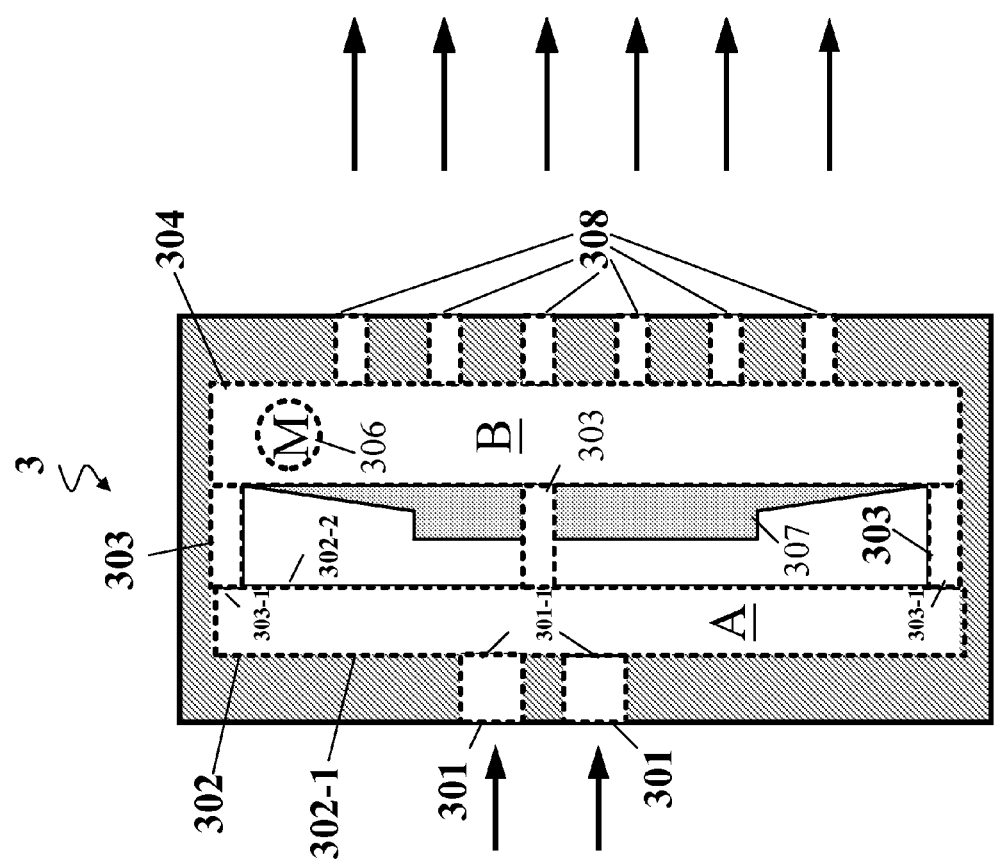
FIG. 2B is a cross-sectional diagram of a noise attenuation device in accordance with another example of the present invention.

FIG. 2B is a cross-sectional diagram of a noise attenuation device 3 in accordance with another example of the present invention. Referring to FIG. 2B, the noise attenuation device 3 may include a number of (in the example, two) first tubes 301, a first housing 302, a number of (in the example, three) second tubes 303, a second housing 304, a microphone 306, a speaker 307 and a number of (in the example, six) third tubes 308. The noise attenuation device 3 may be similar to the noise attenuation device 2 described and illustrated with reference to FIG. 2A except that, for example, the microphone 306 may be disposed near an upper portion within the second housing 304. In an example of the present invention, one end 301-1 of each of the first tubes 301 may contact an outer wall 302-1 of the first housing 302 at a first region (not numbered) with a first area, and one end 303-1 of each of the second tubes 303 may contact a second outer wall 302-2 of the first housing 302 at a second region (not numbered) with a second area. In one example of the present invention, the area of the first outer wall 302-1 may be greater than a sum of the first areas and the area of the second outer wall 302-2 may be greater than a sum of the second areas. In another example of the present invention, the ratio of the area of the first outer wall 302-1 to the sum of the first areas may range from approximately 30 to 300. Each of the first tubes 301 and the second tube 303 may be approximately 1 mm in length but may be longer or shorter. The first housing 302 and the second housing 304 may be approximately 1 mm in width but may be thinner or thicker. The volume of the chamber enclosed by the second housing 304 may be kept relatively small. The number of the first tubes 301, the second tubes 303 or the third tubes 308 may vary to fit other applications.

Figure 3A:
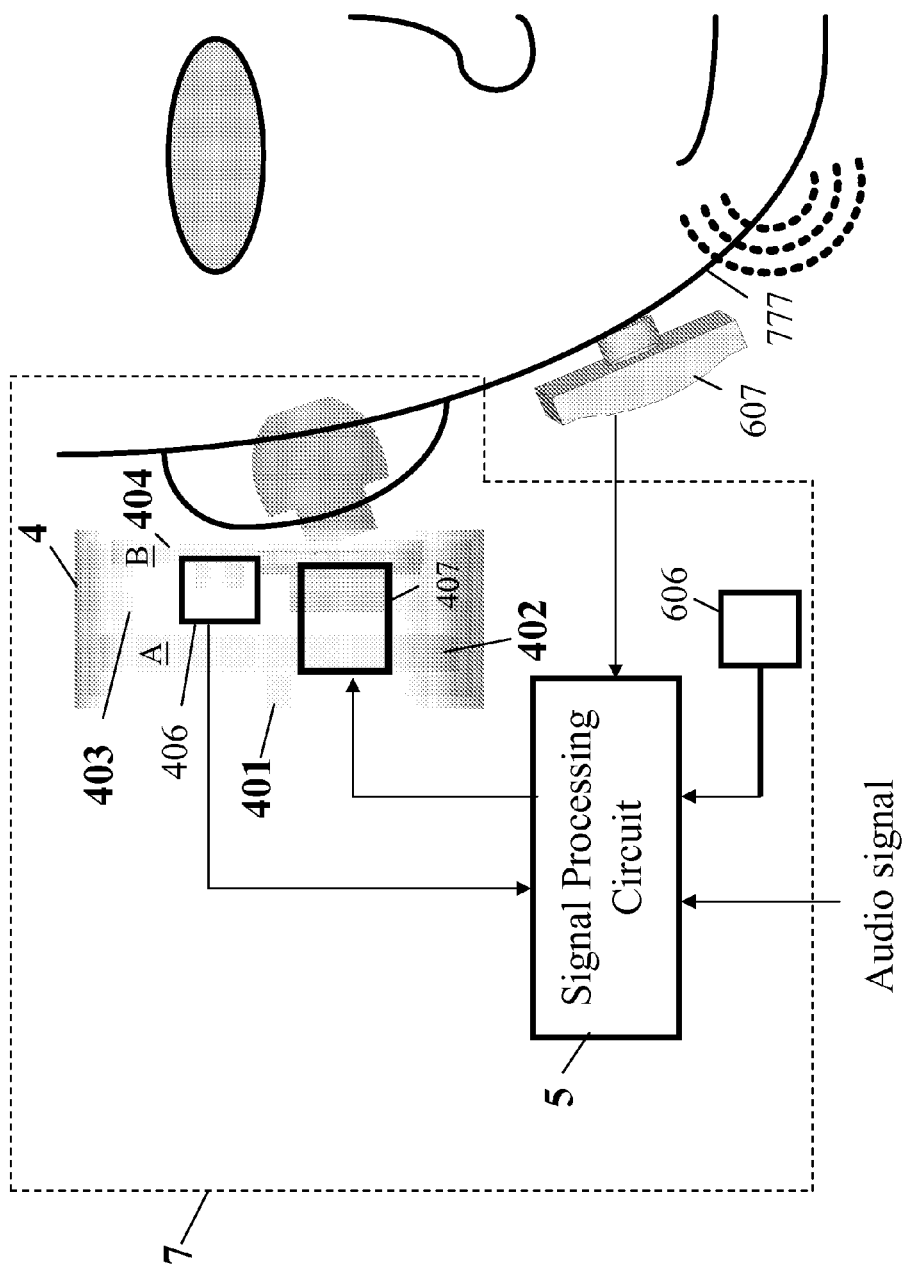
FIG. 3A is a schematic diagram of a noise attenuation device in accordance with an example of the present invention.

FIG. 3A is a schematic diagram of a noise attenuation device 7 in accordance with an example of the present invention. Referring to FIG. 3A, the noise attenuation device 7 may include a noise processing device 4 and a signal processing circuit 5. The noise processing device 4, which may be similar to the noise attenuation devices 1, 2 and 3 respectively described and illustrated with reference to FIGS. 1A, 2A and 2B, may include a first tube 401, a first housing 402, a second tube 403, a second housing 404, a microphone 406 and a speaker 407. The microphone 406 may be disposed at an upper portion of the second housing 404. The noise attenuation device 7 may operate in an environment where noise such as ambient noise may be sensitive to the microphone 406. Noise may denote the intensity, frequency and duration of undesired sounds from a signal source or multiple sources. Furthermore, ambient noise may denote the all-encompassing noise associated with a given environment, which may be a composite of sounds from many sources near and far. The first tube 401, the first housing 402, the second tube 403 and the second housing 404 may function to serve as a low-pass filter to cancel or attenuate high-frequency components of noise higher than, for example, approximately 1 kHz. Furthermore, acoustic signals in the cavity B may be collected by the microphone 406 and then transmitted to the signal processing circuit 5. The signal processing circuit 5 may also receive audio signals from an electronic product, such as a multi-media device or an audio player, by wired or wireless communication. The signal processing circuit 5 may then process the received audio signals and the acoustic signals from the microphone 406 and generate a control signal for controlling the speaker 407.

The noise attenuation device 7 may further include an air-conduction (AC) type microphone 606, which may receive acoustic signals from a user 777. Furthermore, the noise attenuation device 7 may include a bone-conduction (BC) type microphone 607 to receive acoustic signals from the user 777. The received acoustic signals may then be transmitted to the signal processing circuit 5.

Figure 3B:
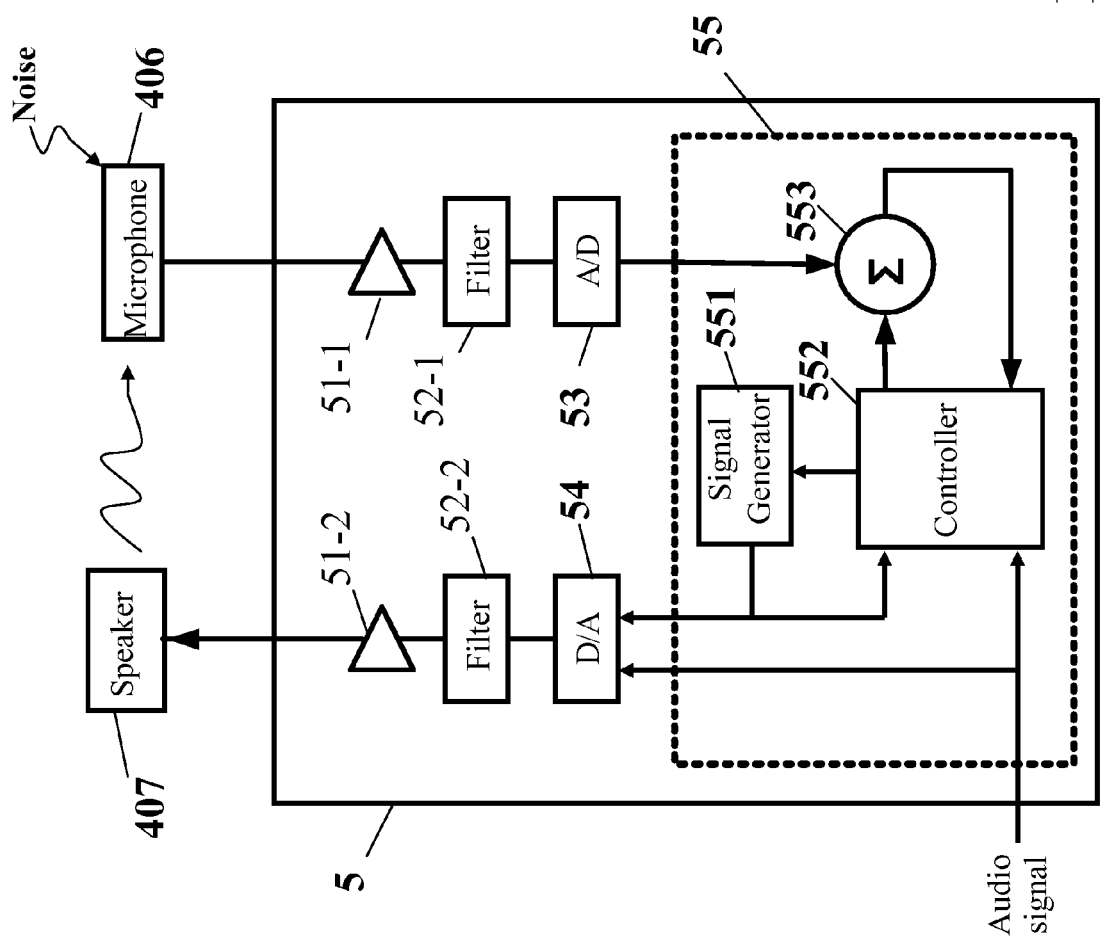
FIG. 3B is a schematic block diagram of a signal processing circuit in accordance with an example of the present invention.

FIG. 3B is a schematic block diagram of the signal processing circuit 5 illustrated in FIG. 3A in accordance with an example of the present invention. Referring to FIG. 3B, the signal processing circuit 5 may include power amplifiers 51-1 and 51-2, filters 52-1 and 52-2, an analog/digital (A/D) converter 53, a digital/analog (D/A) converter 54 and a signal processing module 55. The signals from the microphone 406 may be amplified in the power amplifier 51-1 and then transmitted to the filter 52-1. The filtered signals may then be converted in the A/D converter 53 and input to the signal processing module 55. The signal processing module 55 may include but is not limited to a digital signal processing (DSP) module. The signal processing module 55 may include a mixer 553, a signal generator 551 and a controller 552. Assuming that the microphone 406 may receive a first signal, of which the high-frequency components may be filtered off by the low-pass filter structure, in response to the first signal, the controller 552 may control the signal generator 551 to generate a default signal to drive the speaker 407. The speaker 407 may then provide a second signal, for example, an acoustic signal, which may be subsequently received by the microphone 406. The second signal received by the microphone 406 may be transmitted to the mixer 553 after processed by the power amplifier 51-1, the filter 52-1 and the A/D converter 53. The mixer 553 may combine a converted second signal from the A/D converter 53 and a reference signal from the controller 552 to form a mixed signal. The controller 552 may provide a control signal based on the audio signal from the electronic product, the mixed signal from the mixer 553 and a feedback signal from the signal generator 551. Once the control signal is determined, the controller may send another reference signal to the mixer 553. The audio signal from the electronic product and an output signal from the signal generator 551 may be converted in the D/A converter 54, processed in the filter 52-2 and amplified by the power amplifier 51-2 before transmitted to the speaker 407. An amplified signal from the amplifier 51-2 may drive the speaker 407 to generate a third signal that may offset the noise signal in the cavity B. The operation in the circuit shown in FIG. 3B may be repeated till the controller 552 detects that an output of the mixer 553 may match a predetermined value, which in turn may result in an output signal from the speaker 407 that is able to cancel out the noise in the cavity B.

Figure 4A:
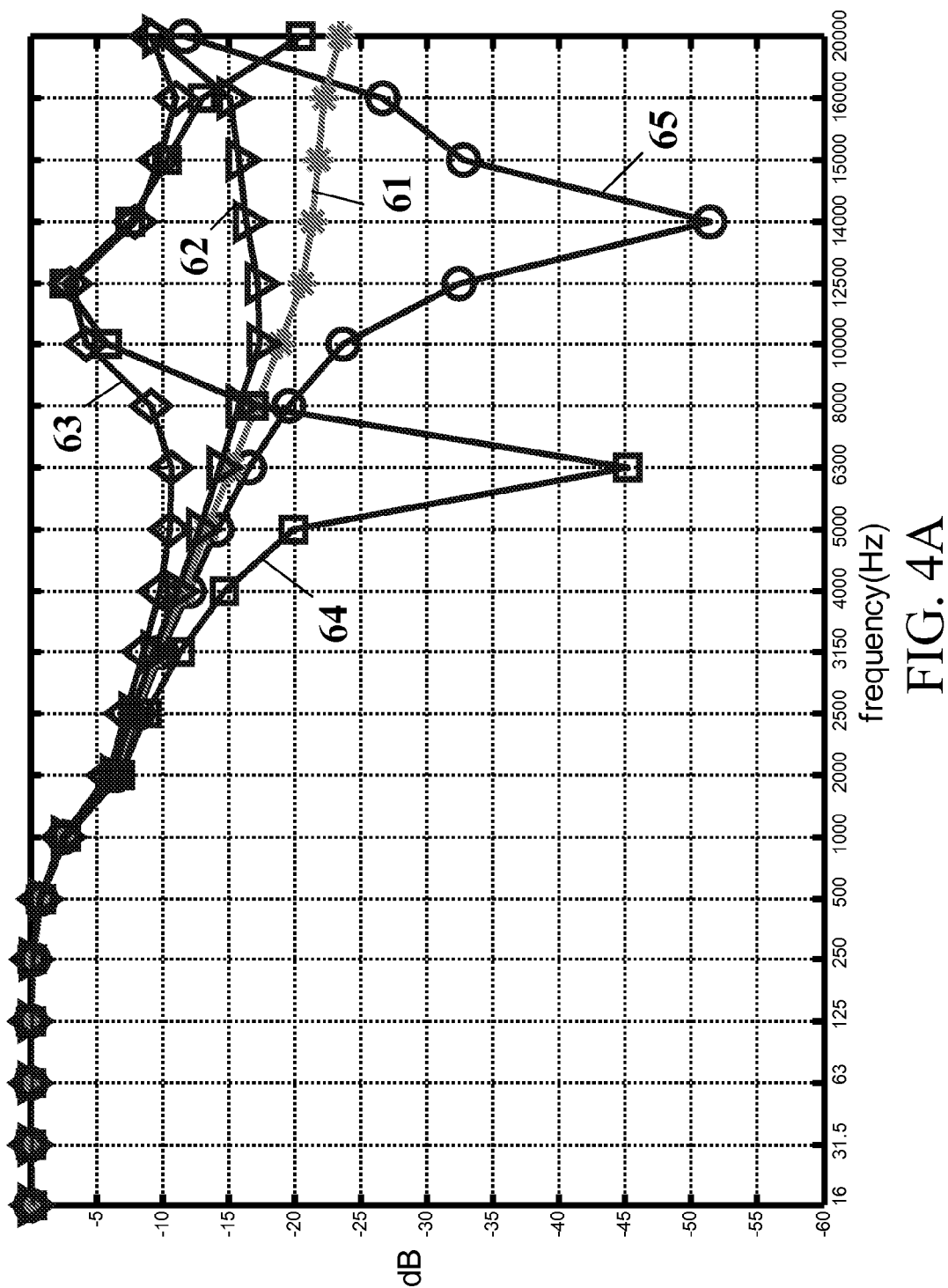
FIG. 4A is a plot showing experimental results of the frequency response each of noise attenuation devices with different arrangements.

FIG. 4A is a plot showing experimental results of the frequency response each of noise attenuation devices with different arrangements to acoustic signals at various frequencies. Referring to FIG. 4A, a curve 61 may represent a frequency response of a desirable noise attenuation device, wherein a first housing may have a cross-sectional area of approximately 15×5 mm² with a width of approximately 3 mm, and the diameter of a first tube may be approximately 1.5 mm such that the ratio of the cross-sectional area of the first housing to that of the first tube is approximately 33.3. Furthermore, the curves 62, 63, 64, and 65 may respectively represent the frequency response in a second housing of the noise attenuation devices described and illustrated with reference to FIGS. 1C, 1D, 1E and 1F, given the same size of the first housing and the first tube and the same area ratio. It may be found from FIG. 4A that the noise attenuation device illustrated in FIG. 1F represented by the curve 65 may have the best noise suppressing effect among the devices at the high-frequency region.

Figure 4B:
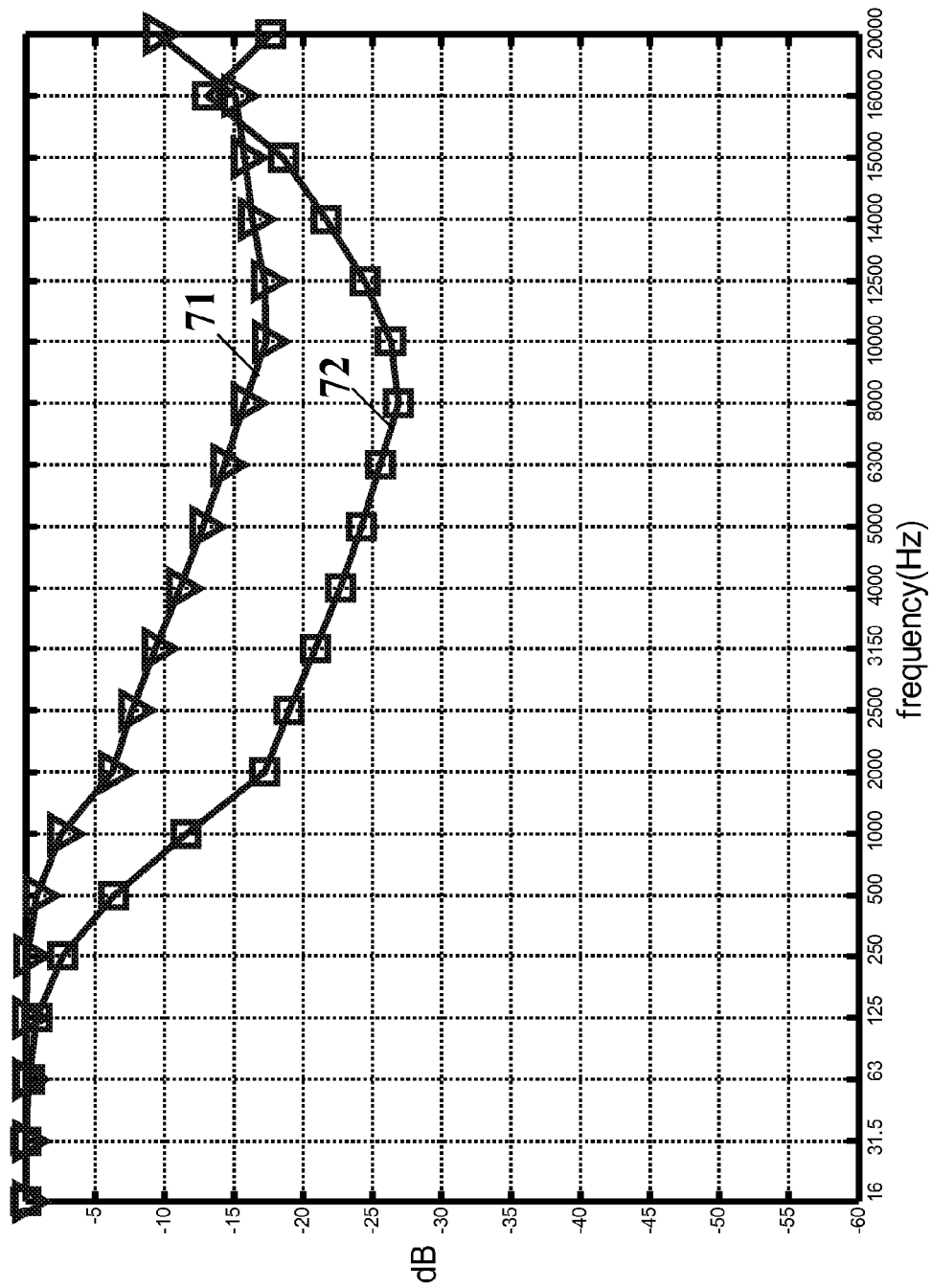
FIG. 4B is a plot showing experimental results of the frequency response each of noise attenuation devices of different sizes.

FIG. 4B is a plot showing experimental results of the frequency response each of noise attenuation devices of different sizes to acoustic signals at various frequencies. Referring to FIG. 4B, a first curve 71 and a second curve 72 may represent a frequency response in a first noise attenuation device having a first size and a second noise attenuation device having a second size, respectively. The first and second noise attenuation devices may be similar to the noise attenuation device 1 described and illustrated with reference to FIG. 1C. In the first noise attenuation device, the first housing may have a cross-sectional area of approximately 15×5 mm² with a width of approximately 3 mm, and the diameter of the first tube may be approximately 1.5 mm. In the second noise attenuation device, the first housing may have a cross-sectional area of approximately 20×15 mm² with a width of approximately 3 mm, and the diameter of the first tube 101 may be approximately 1.5 mm. Accordingly, the second noise attenuation device may have a greater area ratio than the first noise attenuation device. It may be found from FIG. 4B that the second noise attenuation device represented by the curve 72 may have better noise suppressing effect than the first noise attenuation devices because of the larger area ratio.

Figure 4C:
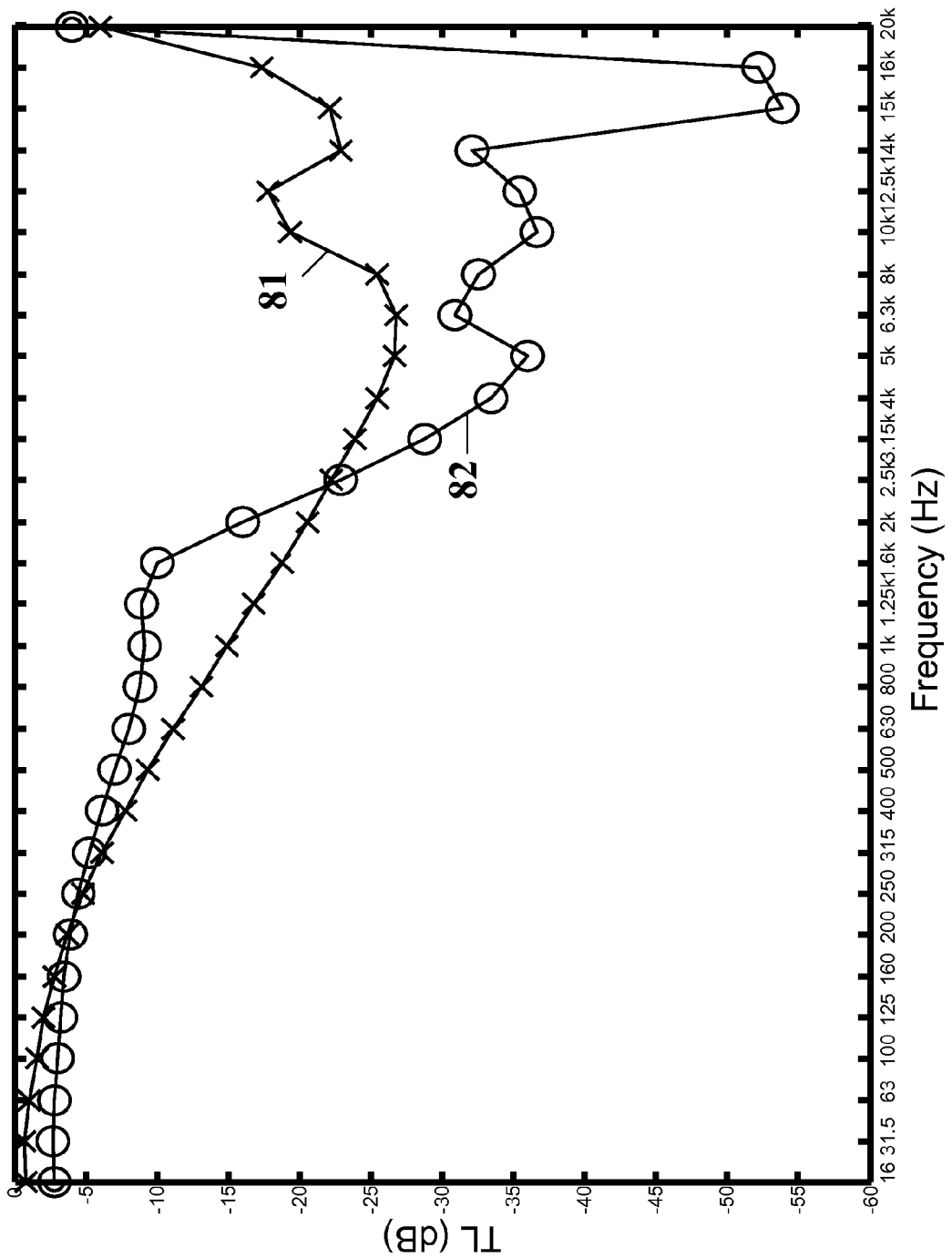
FIG. 4C is a plot showing experimental results of the frequency response each of noise attenuation devices with different chamber designs.

FIG. 4C is a plot showing experimental results of the frequency response each of noise attenuation devices with different chamber designs to acoustic signals at various frequencies. Referring to FIG. 4C, a first curve 81 may represent a frequency response in a first noise attenuation device with a single chamber, for example, the chamber A, while a second curve 82 may represent a frequency response in a second noise attenuation device with two chambers such as the chambers A and B described and illustrated with reference to FIG. 2A. It may be found from FIG. 4C that the second noise attenuation device represented by the curve 82 may have better noise suppressing effect than the first noise attenuation devices because of the addition of the second chamber B.

It will be appreciated by those skilled in the art that changes could be made to the preferred embodiments described above without departing from the broad inventive concept thereof. It is understood, therefore, that this invention is not limited to the particular embodiments disclosed, but is intended to cover modifications within the spirit and scope of the present application as defined by the appended claims.

I claim:

1. A noise attenuation device comprising:
a first tube for receiving an acoustic signal;
a first housing defining a first cavity between a first surface having an area and a second surface having an area, the first tube being coupled to the first housing at the first surface for conducting the acoustic signal into the first cavity, wherein one end of the first tube contacts the first surface at a first region with a first area;
a second housing defining a second cavity between a first surface and a second surface;
a speaker positioned between the first housing and the second housing; and
a second tube coupled between the second surface of the first housing and the first surface of the second housing for conducting the acoustic signal between the first cavity and the second cavity, wherein one end of the second tube contacts the second surface of the first housing at a second region with a second area,
wherein the first tube, the first housing and the second tube form a filter structure, and the area of the first surface of the first housing is greater than the first area and the area of the second surface of the first housing is greater than the second area.

2. The noise attenuation device of claim 1 further comprising a third tube coupled to the second surface of the second housing for conducting the acoustic signal.

3. The noise attenuation device of claim 2 further comprising an earplug surrounding and encompassing the circumference of the third tube.

4. The noise attenuation device of claim 1, wherein a ratio of the area of the first surface of the first housing to the first area is equal to or greater than 30.

5. The noise attenuation device of claim 1, wherein a ratio of the area of the first surface of the first housing to the first area is equal to or smaller than 300.

6. The noise attenuation device of claim 1 further comprising at least one microphone near the second housing.

7. The noise attenuation device of claim 1, wherein the first tube, the first housing, the second tube and the second housing form another filter structure for the noise attenuation device.

8. A noise attenuation device comprising: a noise processing device comprising:
a first tube for receiving an acoustic signal;
a first housing defining a first cavity between a first surface having an area and a second surface having an area, the first tube being coupled to the first housing at the first surface for conducting the acoustic signal into the first cavity, wherein one end of the first tube contacts the first surface at a first region with a first area;
a second housing defining a second cavity between a first surface and a second surface; and
a second tube coupled between the second surface of the first housing and the first surface of the second housing for conducting the acoustic signal between the first cavity and the second cavity, wherein one end of the second tube contacts the second surface of the first housing at a second region with a second area,
wherein the area of the first surface of the first housing is greater than the first area and the area of the second surface of the first housing is greater than the second area so as to attenuate noise in the second cavity;
a first microphone;
a speaker electrically coupled to the second housing; and
a signal processing circuit electrically coupled to the first microphone and the speaker.

9. The noise attenuation device of claim 8 further comprising a second microphone electrically coupled to the signal processing circuit.

10. The noise attenuation device of claim 9, wherein the second microphone includes at least one of an air-conduction (AC) type microphone or a bone-conduction (BC) type microphone.

11. The noise attenuation device of claim 8, wherein the signal processing circuit provides a signal to offset the noise.

12. The noise attenuation device of claim 8, wherein the noise processing device further comprises a third tube coupled to the second surface of the second housing for conducting the acoustic signal.

13. The noise attenuation device of claim 8, wherein the ratio of the area of the first surface of the first housing to the first area is equal to or greater than 30.

14. The noise attenuation device of claim 8, wherein the ratio of the area of the first surface of the first housing to the first area is equal to or smaller than 300.

15. The noise attenuation device of claim 8, wherein the speaker includes a speaker chamber isolated from the first housing and a speaker device within the speaker chamber coupled to the second housing.

16. The noise attenuation device of claim 8, wherein the first microphone is acoustically coupled to the second housing.

17. A noise attenuation device comprising:
   at least one first tube for receiving an acoustic signal;
   a first housing defining a first cavity between a first surface having an area and a second surface having an area, the at least one first tube being coupled to the first housing at the first surface for conducting the acoustic signal into the first cavity, wherein one end of each of the at least one first tube contacts the first surface at a first region with a first area;
   a second housing defining a second cavity between a first surface and a second surface; and
   at least one second tube coupled between the second surface of the first housing and the first surface of the second housing for conducting the acoustic signal between the first cavity and the second cavity, wherein one end of each of the at least one second tube contacts the second surface of the first housing at a second region with a second area,
   wherein a ratio of the area of the first surface of the first housing to a sum of the first area of each of the at least one first tube and a ratio of the area of the second surface of the first housing to a sum of the second area of each of the at least one second tube are selected to attenuate noise over a predetermined frequency level.

18. The noise attenuation device of claim 17, wherein the ratio of the area of the first surface of the first housing to the sum of the first area of each of the at least one first tube is equal to or greater than 30.

19. The noise attenuation device of claim 17, wherein the ratio of the area of the first surface of the first housing to the sum of the first area of each of the at least one first tube is equal to or smaller than 300.

20. The noise attenuation device of claim 17, wherein one of the at least one first tube is disposed near a center portion of the first surface of the first housing, and one of the at least one of second tube is disposed near a center portion of the second surface of the first housing.

21. The noise attenuation device of claim 17, wherein one of the at least one first tube is disposed near an upper portion of the first surface of the first housing, and one of the at least one of second tube is disposed near a lower portion of the second surface of the first housing.

22. The noise attenuation device of claim 17, wherein one of the at least one first tube is disposed near an upper portion of the first surface of the first housing, and one of the at least one of second tube is disposed near an upper portion of the second surface of the first housing.

* * * * *